United States Patent [19]
Elgas et al.

[11] Patent Number: 5,858,233
[45] Date of Patent: Jan. 12, 1999

[54] TRANSITION MANIFOLD FOR BLOOD OXYGENATOR APPARATUS

[75] Inventors: Roger J. Elgas, Anaheim Hills; Robert F. Gremel, Huntington Beach, both of Calif.; Robert Cushing Hamlen, St. Paul, Minn.

[73] Assignee: Medtronic, Inc., Minneapolis, Minn.

[21] Appl. No.: 586,163

[22] Filed: Jan. 11, 1996

[51] Int. Cl.$^6$ .............................. B01D 61/00; A61M 1/14
[52] U.S. Cl. .............................. 210/456; 210/477; 422/45
[58] Field of Search .............................. 210/232, 321.81, 210/321.89, 420, 421, 456, 474, 477, 482; 422/44, 45, 46, 48

[56] References Cited

U.S. PATENT DOCUMENTS

| | | | |
|---|---|---|---|
| 2,742,849 | 4/1956 | Stiglitz | 210/477 |
| 2,784,843 | 3/1957 | Braunlich | 210/456 |
| 3,712,474 | 1/1973 | Martinez | 210/456 |
| 4,904,384 | 2/1990 | Potz | 210/420 |
| 4,964,984 | 10/1990 | Reeder et al. | 210/456 |
| 4,975,247 | 12/1990 | Badolato et al. | 422/48 |
| 5,076,922 | 12/1991 | DeAre | 210/474 |
| 5,188,732 | 2/1993 | De Niel et al. | 210/456 |
| 5,304,305 | 4/1994 | Lehrer | 210/474 |

OTHER PUBLICATIONS

Maxima Hollow Fiber Membrane Oxygenator—four page brochure (undated) by Medtronic.
Minimax Plus Oxygenation Systems—five page brochure (undated) by Medtronic.

*Primary Examiner*—John Kim
*Attorney, Agent, or Firm*—Michael H. Jester

[57] ABSTRACT

A transition manifold is provided for use in association with the upper end of a generally cylindrical heat exchanger fiber bundle having a plurality of vertically extending conduits with open upper ends terminating in substantially co-planar fashion. The transition manifold is specially configured for redirecting blood flowing out of the upper end of the heat exchanger fiber bundle radially outwardly around the fibers of a concentric, surrounding oxygenator fiber bundle. The transition manifold includes a generally conical wall member defining a surface which extends at a relatively flat angle with respect to a plane perpendicular to a vertical central axis of the heat exchanger fiber bundle. The surface of the conical wall member diverges away from the upper end of the heat exchanger fiber bundle in a direction moving radially outwardly from the central axis. The transition manifold spreads the blood substantially uniformally around an upper portion of the generally cylindrical oxygenator fiber bundle while minimizing shear forces that traumatize blood cells and platelets and minimizing recirculations which can lead to clotting.

7 Claims, 10 Drawing Sheets

TRANSITION MANIFOLD FOR BLOOD OXYGENATOR APPARATUS

BACKGROUND OF THE INVENTION

The present invention relates to surgical support apparatus, and more particularly to a component of an improved blood oxygenator used to maintain a patient's blood at a predetermined temperature while replacing carbon dioxide in the blood with oxygen.

Blood oxygenators are well known in the medical field. Typically they are disposable components of so-called "heart-lung machines." These machines mechanically pump a patient's blood and oxygenate the blood during major surgery such as a heart bypass operation. A typical commercially available blood oxygenator includes a heat exchanger and a membrane-type oxygenator. The patient's blood is continuously pumped through the heat exchanger. A suitable heat transfer fluid such as water is also pumped through the heat exchanger, separated from the blood but in heat transfer relationship therewith. The water is either heated or cooled externally flow the blood oxygenator to maintain the patient's blood at a predetermined desired temperature. The membrane oxygenator comprises a so-called "bundle" of thousands of tiny hollow fibers made of a special polymer material having microscopic pores. Blood exiting the heat exchanger flows around the outside surfaces of these fibers. At the same time an oxygen-rich, as mixture, sometimes including, anesthetic agents, flows through the hollow fibers. Due to the relatively high concentration of carbon dioxide in the blood arriving from the patient carbon dioxide from the blood diffuses through the microscopic pores in the fibers and into the gas mixture. Due to the relatively low concentration of oxygen in the blood arriving from the patient oxygen from the gas mixture diffuses through the microscopic pores in the fibers into the blood. The oxygen content of the blood is raised, and its carbon dioxide content is reduced. The blood is also heated or cooled before being returned to the patient.

A blood oxygenator must have a sufficient volumetric flow rate to allow proper temperature control and oxygenation. However, blood is typically in short supply and is very expensive. Therefore, it is desirable to minimize the volume of blood contained within the oxygenator, preferably to less than five hundred cubic centimeters. The cells and platelets in human blood are delicate and can be traumatized if subjected to excessive shear forces. Therefore the blood flow velocity inside a blood oxygenator must not be excessive. In addition the configuration and geometry of the inlet nozzle, manifolds and outlet nozzle of the blood flow path for a given blood flow rate must not create re-circulations (eddies) or stagnant areas that can lead to clotting.

Once the blood has flowed through the heat exchanger it needs to be redirected around the thousands of fibers of the membrane oxygenator in an efficient and uniform manner. This requires some sort of transition manifold with an optimum geometry and configuration.

SUMMARY OF THE INVENTION

Accordingly, it is the primary object of the present invention to provide a manifold that is optimally configured for directing blood flowing out of a heat exchanger into a surrounding membrane-type oxygenator.

In accordance with the present invention, a transition manifold is provided for use in association with the upper end of a generally cylindrical heat exchanger fiber bundle having a plurality of vertically extending conduits with open upper ends terminating in substantially co-planar fashion. The transition manifold is specially configured for redirecting blood flowing out of the upper end of the heat exchanger fiber bundle radially outwardly around the fibers of a concentric, surrounding oxygenator fiber bundle. The transition manifold includes a generally conical wall member defining a surface which extends at a relatively flat angle with respect to a plane perpendicular to a vertical central axis of the heat exchanger fiber bundle. The surface of the conical wall member diverges away from the upper end of the heat exchanger fiber bundle in a direction moving, radially outwardly from the central axis. The transition manifold spreads the blood substantially uniformly around an upper portion of the generally cylindrical oxygenator fiber bundle while minimizing shear forces that traumatize blood cells and platelets and minimizing recirculations which can lead to clotting.

BRIEF DESCRIPTION OF THE DRAWINGS

The following drawing figures illustrate a preferred embodiment of the present invention. Throughout the drawing figures, like reference numerals refer to like parts.

DETAILED DESCRIPTION OF THE PREFERRED EMBODIMENT

Figure 1:
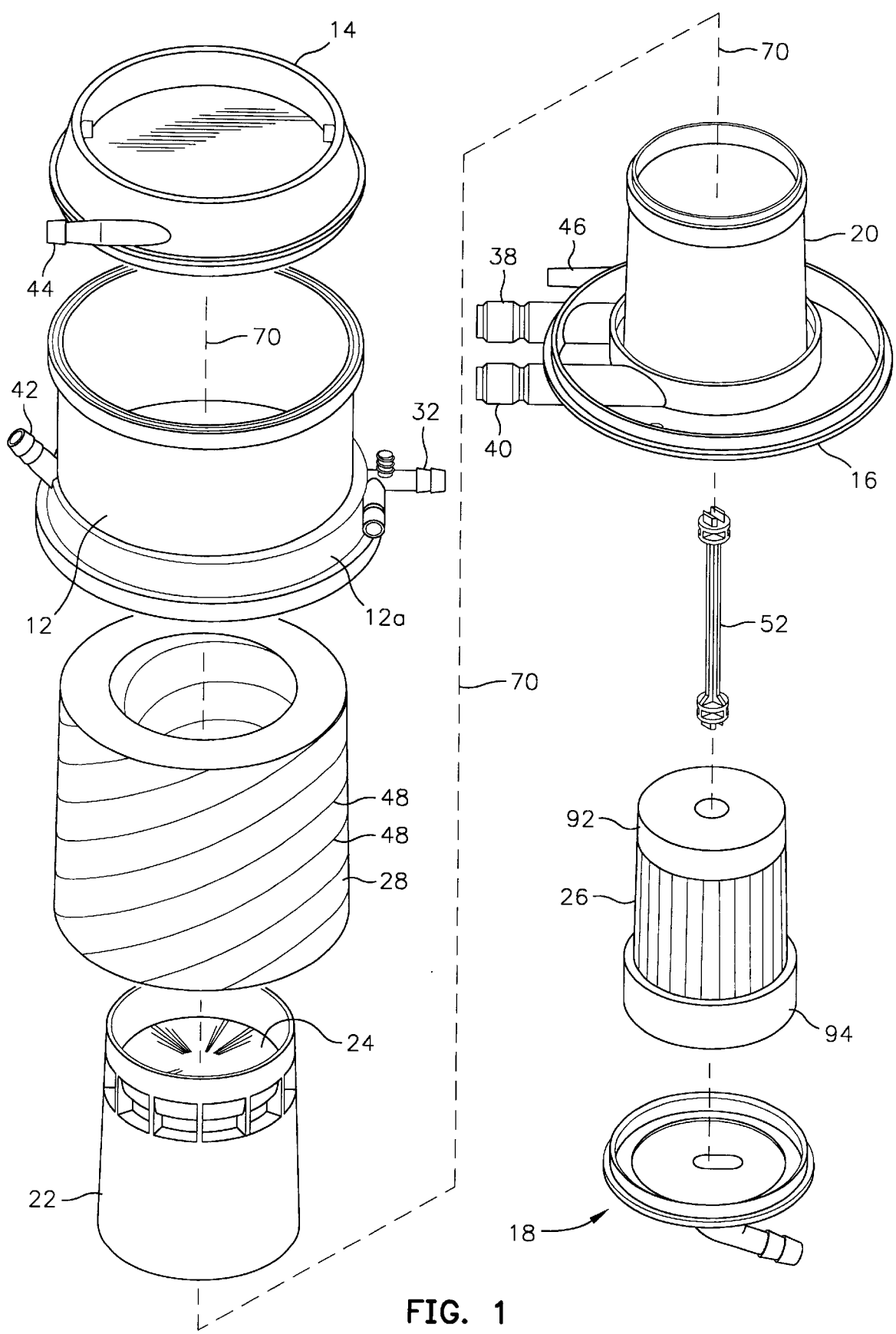
FIG. 1 is an exploded isometric view of a blood oxygenator constructed in accordance with the present invention.
Figure 2:
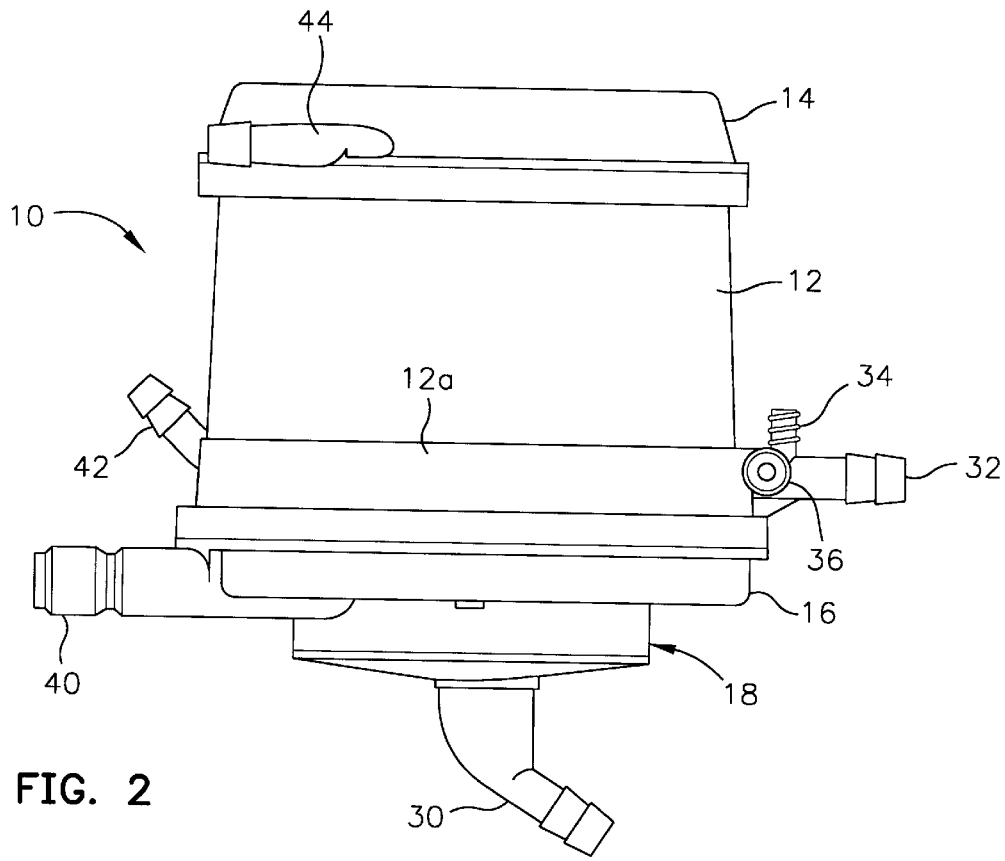
FIG. 2 is a side elevation view of the blood oxygenator.
Figure 3:
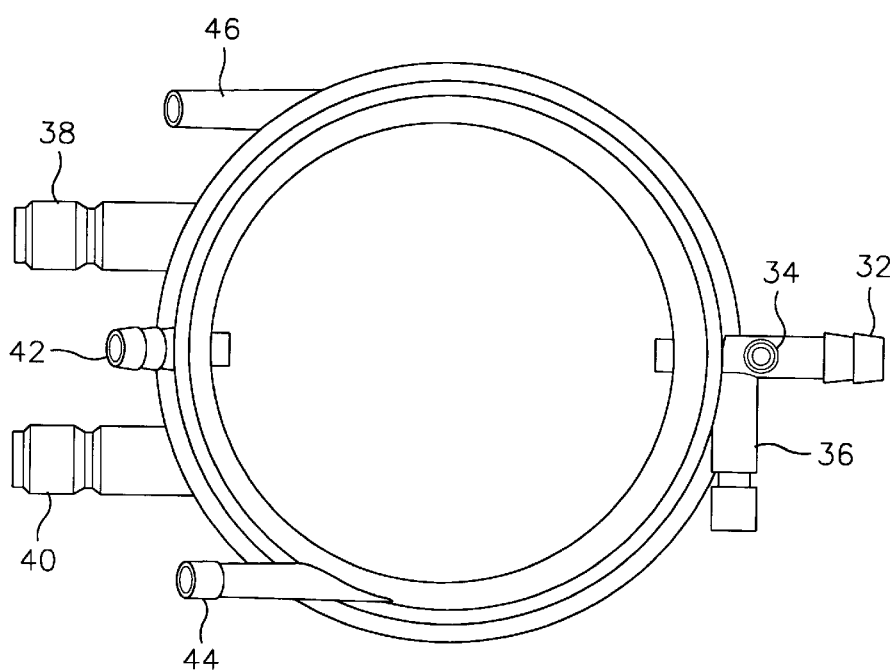
FIG. 3 is a top plan view of the blood oxygenator.

Referring to FIGS. 1–3, blood oxygenator 10 constructed in accordance with the present invention comprises an outer generally cylindrical vessel 12 which is sealed at its upper end by a generally saucer-shaped upper hollow venous gas header 14. The lower end of the vessel 12 is sealed by a generally saucer-shaped lower hollow venous gas header 16. A blood inlet manifold 18 is connected to the center of the underside of the lower venous gas header 16. Concentric, generally cylindrical inner and outer heat exchanger housings 20 and 22 are connected at their lower ends to the center of the lower venous header 16. The upper end of the outer heat exchanger housing 22 includes a transition manifold 24. The interior of the inner heat exchanger housing 20 surrounds and encloses a generally cylindrical first fiber bundle 26 made up of a plurality of vertically oriented hollow micro-conduits. These micro-conduits convey blood vertically therethrough in an upward direction. A second generally cylindrical fiber bundle 28 concentrically surrounds the outer heat exchanger housing 22 and is positioned inside the inner wall of the cylindrical vessel 12. The upper and lower ends of the generally ring-shaped second fiber bundle 28 communicate with the upper and lower venous gas headers 14 and 16, respectively.

The blood inlet manifold 18 (FIG. 2) includes a barbed blood inlet nozzle 30 which bends downwardly at an angle relative to the central vertical axis of the vessel 12. A barbed blood outlet nozzle 32 (FIGS. 2 and 3) extends horizontally from the exterior of an enlarged or flared portion 12a of the vessel 12. A standard leur fitting 34 (FIG. 2) extends vertically from the base of the blood outlet nozzle 32. A thermometer probe fitting 36 (FIG. 3) extends horizontally from the base of the blood outlet nozzle 32.

Inlet and outlet nozzles 38 and 40 (FIGS. 1 and 3) for a heat transfer fluid such as water extend horizontally from one side of the low venous gas header 16 and communicate with water flow passages inside the inner heat exchanger housing 20. A barbed de-bubbler nozzle 42 (FIG. 2) extends upwardly at an angle from the flared portion 12a of the vessel 12. A gas mixture inlet nozzle 44 (FIGS. 1, 2 and 3) extends horizontally from the periphery of the upper venous gas header 14. A gas mixture outlet nozzle 46 (FIGS. 1 and 3) extends from the periphery of the lower venous gas header 16 parallel to the water inlet and outlet nozzles 38 and 40.

Figure 4:
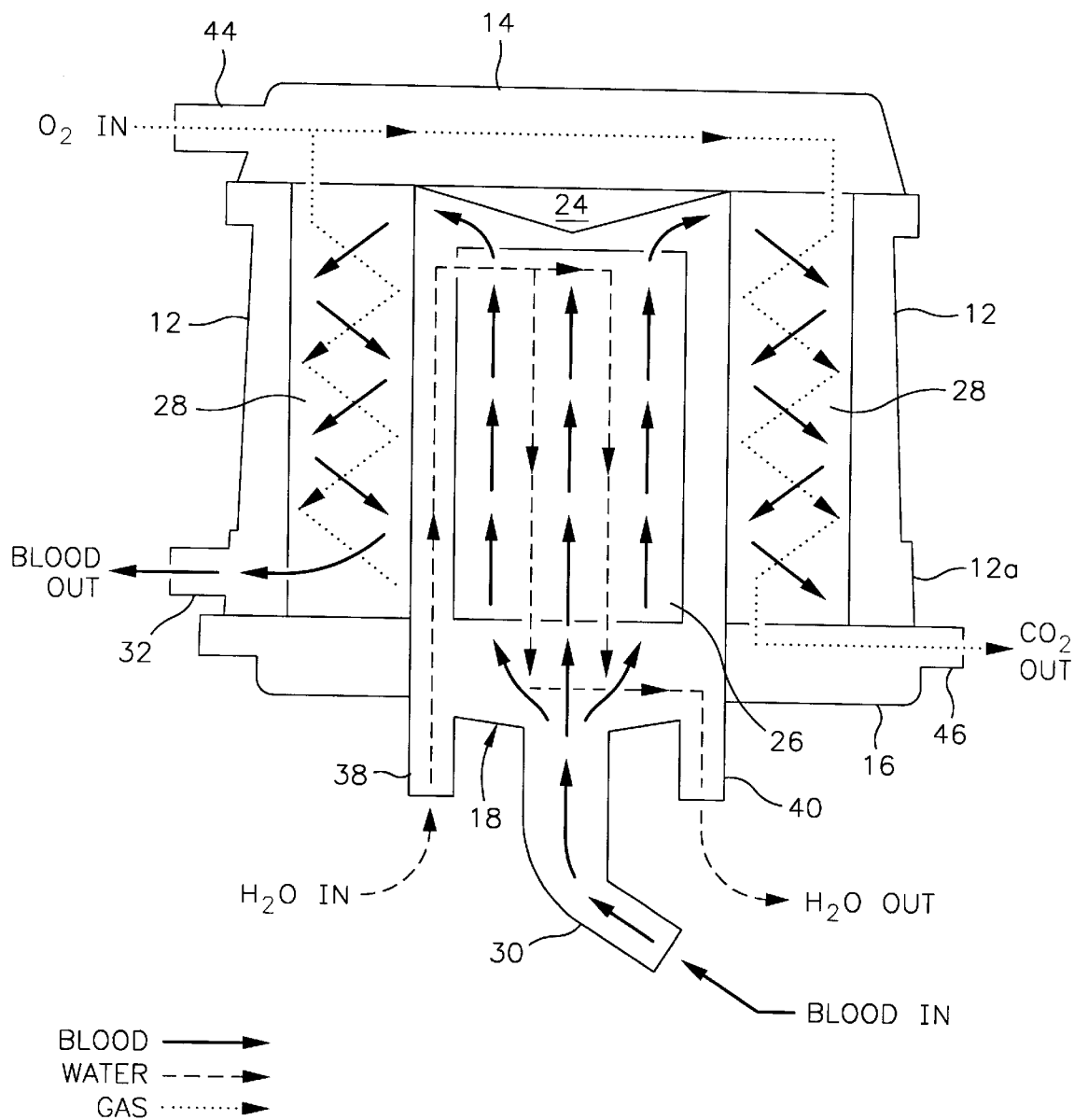
FIG. 4 is a diagrammatic view illustrating the blood, heat transfer fluid and gas mixture flow paths of the blood oxygenator.

The blood, heat transfer fluid and gas mixture flow paths of the blood oxygenator 10 can best be understood by way of reference to the diagrammatic vertical sectional view of FIG 4. In that figure the flow of blood is illustrated diagrammatically by the bold solid arrows. The flow of heat transfer fluid (water) is illustrated by the dashed lines. The flow of gas mixture is illustrated by the sequence of dots. Blood from the patient flows through tubing, (not illustrated) connected to the blood inlet nozzle 30. This incoming blood spreads out through the blood inlet manifold 18 and travels vertically in an upward direction through the micro-conduits of the first fiber bundle 26 of the central heat exchanger that forms the core of the blood oxygenator 10. Water flows in through the inlet nozzle 38 vertically upward to the top of the heat exchanger fiber bundle 26 through a separate channel isolated from the fiber bundle 26. The water is then directed downwardly and across the outside of the micro-conduits of the fiber bundle 26. The water flows around the outside of the micro-conduits in a direction opposite to the direction of flow of the blood within the micro-conduits. The water exiting from the lower end of the first fiber bundle 26 exits through the outlet nozzle 40. The water is heated or cooled outside the blood oxygenator, as necessary to regulate the temperature of the blood flowing through the micro-conduits of the heat exchanger. The use of a counter-flow heat exchanger provides optimum heat exchange efficiency. The temperature of the blood can be monitored by a circuit (not illustrated) that includes a thermister or other temperature sensing device (not illustrated) mounted inside the thermometer probe fitting 36 (FIGS. 2 and 3).

Blood exiting from the upper end of the first fiber bundle 26 (FIG. 4) of the heat exchanger is directed radially outwardly by the transition manifold 24. This blood then travels around the outside of the fibers of the second fiber bundle 28 that forms the membrane oxygenator. The blood travels downwardly past the outside surfaces of the fibers of the second fiber bundle 28. When the blood reaches the lower portion of the second fiber bundle 28, it is collected in an outlet manifold defined by the flared portion 12a of the vessel and exits through the blood outlet nozzle 32. The blood outlet nozzle 32 is connected to tubing (not illustrated) for returning the blood to the patient.

A gas mixture rich in oxygen from a pressurized source (not illustrated) is conveyed through a hose (not illustrated) through the gas mixture inlet nozzle 44, and into the upper venous gas header 14. The upper gas header 14 communicates with the upper ends of the fibers in the second fiber bundle 28 forming the membrane oxygenator. The oxygen-rich gas mixture travels down through the interior of the fibers in the fiber bundle 28. These fibers are micro-porous. Carbon dioxide from the blood surrounding the fibers in the bundle 28 diffuses through the walls of the fibers into the gas mixture. Similarly, oxygen from the gas mixture inside the fibers of the bundle 28 diffuses through the micro-pores into the blood.

The gas mixture now having an elevated carbon dioxide content exits the lower ends of the fibers of the second fiber bundle 28 into the lower venous gas header 16 and then exits therefrom via the gas mixture outlet nozzle 46. This gas mixture now has a lowered oxygen content. The nozzle 46 is connected to another gas hose (not illustrated).

Figure 5:
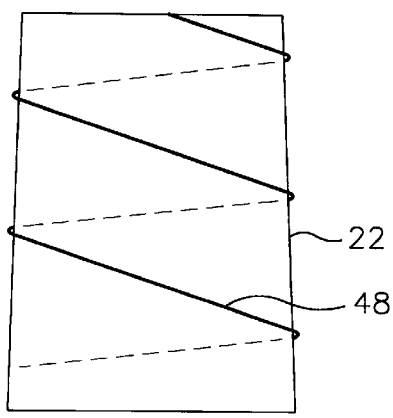
FIG. 5 is a diagrammatic view illustrating the fabrication of the oxygenator fiber bundle of the blood oxygenator.

FIG. 5 is a diagrammatic illustration of the fabrication of the second fiber bundle 28 that forms the membrane oxygenator of the preferred embodiment 10. The second fiber bundle 28 is comprised of thousands of discrete fibers 48 wound in spiral fashion from the top to the bottom and then back again around the heat exchanger housing 22. This is illustrated diagrammatically by the solid and dashed lines in FIG. 5 which extend at angles relative to the vertical central axis of the housing 22. Each fiber 48 is made of a microporous polymer material as is well known in the art. The microscopic sized pores in the walls of the hollow fibers 48 permit carbon dioxide from the blood surrounding the outside of the fibers to diffuse into the gas mixture inside of the hollow fibers. Similarly, oxygen from the gas mixture inside the hollow fibers can diffuse through the microscopic pores into the blood surrounding, the outside of the fibers. Oxygenator fiber bundles of this general type are well known and are commercially available from Medtronic Cardiopulmonary of Anaheim, Calif., U.S.A. under the trademarks MAXIMA and MAXIMA PLUS. See also U.S. Pat. No. 4,975,247 of Badolato, et al. assigned to Medtronic, Inc. entitled MASS TRANSFER DEVICE HAVING A MICROPOROUS, SPIRALLY WOUND HOLLOW FIBER MEMBRANE the entire disclosure of which is specifically incorporated herein by reference.

Figure 6:
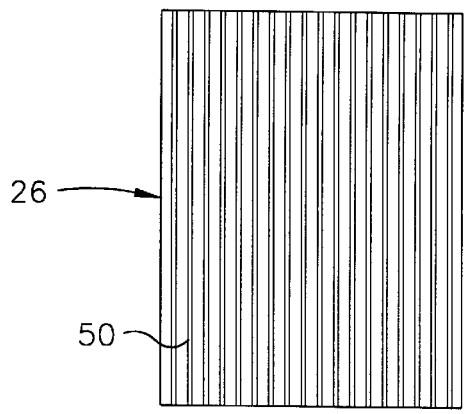
FIG. 6 is a diagrammatic view of the heat exchanger fiber bundle of the blood oxygenator.

FIG. 6 is a diagrammatic illustration of the first fiber bundle 26 which serves as the core of the heat exchanger portion of the blood oxygenator 10. The fiber bundle 26 has a generally cylindrical figuration and comprises approximately five thousand four-hundred vertically (axially) extending hollow fibers 50. Preferably the fibers are provided in the form of a continuous long web of milo-conduit wrapping material in which the fibers are held together by a thin, flexible, horizontally extending woven interconnect (not illustrated). Such wrapping material is commercially available from Mitsubishi Rayon, Co., Ltd. Under the designation HFE430-1 Hollow Fiber. This material uses polyethylene fibers. Similar wrapping material is also commercially available from Hoechst Celanese Corporation under the designation Heat Exchanger Fiber Mat. This material uses polypropylene fibers.

The hollow fibers 50 (FIG. 6) of the heat exchanger fiber bundle 26 have an internal diameter which is so small, e.g. four hundred and twenty-eight microns, that the free flow of blood therethrough, may be impaired due to the presence of trapped air bubbles. Accordingly, before using the heat exchanger, it is desirable to pass a wetting agent through the fibers 50. The wetting agent may comprise an ampiphilic molecule having one end which is hydrophilic and a second end which is hydrophobic. An example of such a compound is hydrogenated phosphatidyl choline commercially available from Naderman Corporation under the trademark PHOSPOLIPON. This material has a USP grade and an FDA master file number, approving it for human intravenous use.

Figure 7:
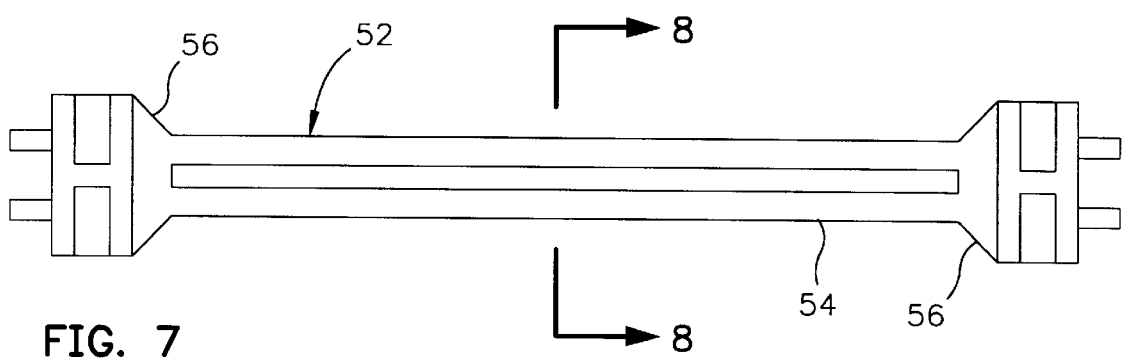
FIG. 7 is an enlarged side elevation view of the spindle of the heat exchanger of the blood oxygenator around which is wound the micro-conduit wrapping material.
Figure 8:
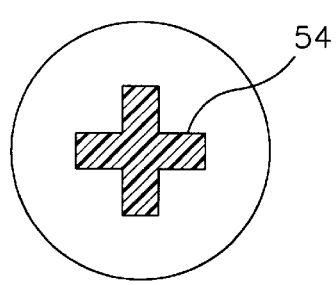
FIG. 8 is a cross-section view of the spindle of FIG. 7 taken along line 8—8 of FIG. 7.
Figure 9:
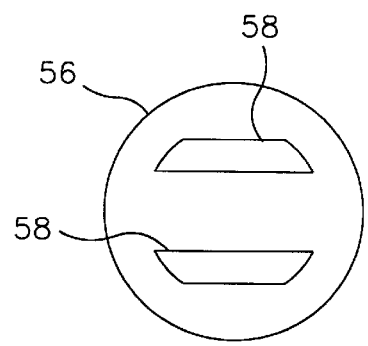
FIG. 9 is an end elevation view of the spindle of FIG. 7 taken from the right end of FIG. 7.
Figure 10:
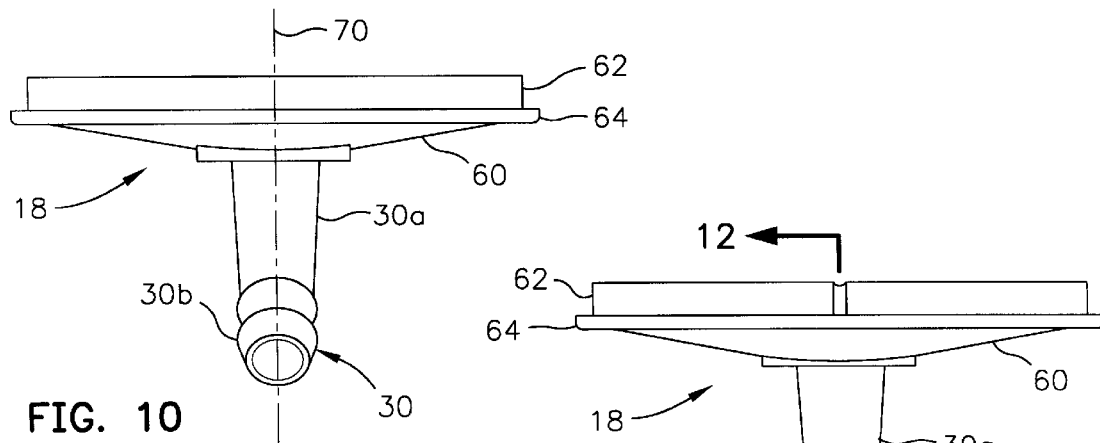
FIG. 10 is an enlarged front elevation view of the blood inlet manifold of the blood oxygenator.
Figure 11:
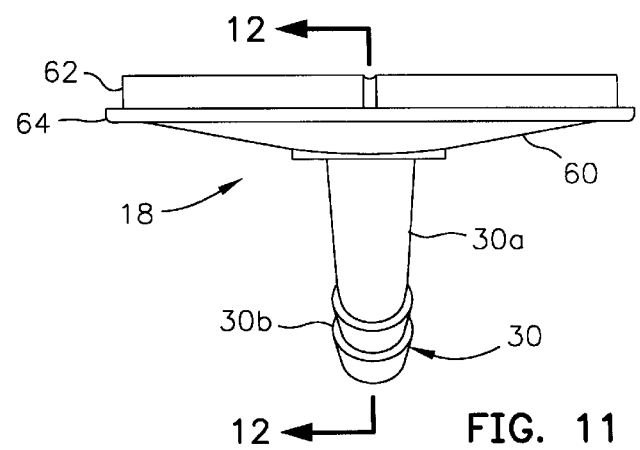
FIG. 11 is an enlarged rear elevation view of the blood inlet manifold of the blood oxygenator.

The micro-conduit wrapping material of the heat exchanger core is wound about a central, vertically orientated elongated spindle 52 (FIG. 7). The spindle 52 has an intermediate segment 54 having a cross-shaped cross-section as best seen in FIG. 8. The spindle 52 has enlarged driving ends 56 connected to the opposite ends of the intermediate segment 54. Each of the driving ends 56 has a pair of parallel extending ribs 58 (FIG. 9) which are used to lock the spindle into a winding machine (not illustrated). This machine utilized to wind the micro-conduit wrapping material about the spindle 52. Preferably the micro-conduit wrapping material is compactly wound about the central spindle 52, but without any Substantial tension on the web.

Further details regarding the wetting agent and construction of the heat exchanger fiber bundle 26 are set forth in co-pending U.S. patent application Ser. No. 08/584,275 entitled BLOOD HEAT EXCHANGE SYSTEM EMPLOYING MICRO-CONDUIT filed on Jan. 11, 1996 and assigned to Medtronic, Inc. of Minneapolis, Minn. United States of America. The entire disclosure of the aforementioned U.S. Patent Application is specifically incorporated herein be reference.

Figure 15:
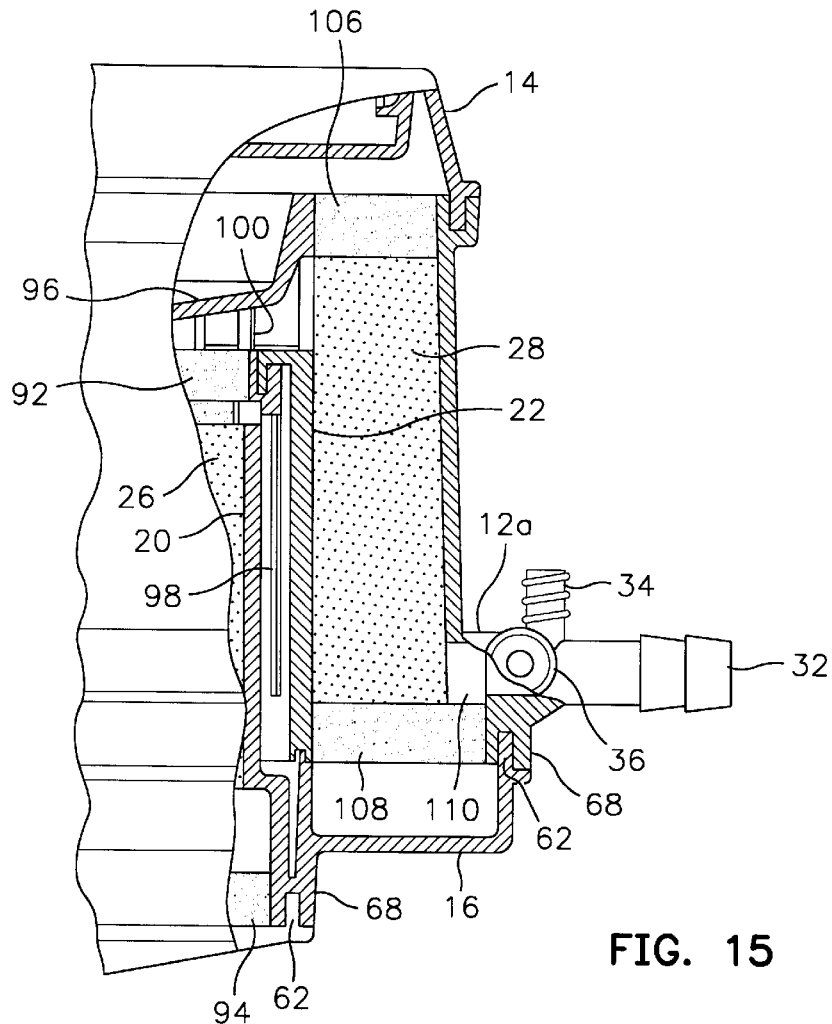
FIG. 15 is an enlarged fragmentary, broken away view illustrating the internal assembly of the components of the blood oxygenator.
Figure 16:
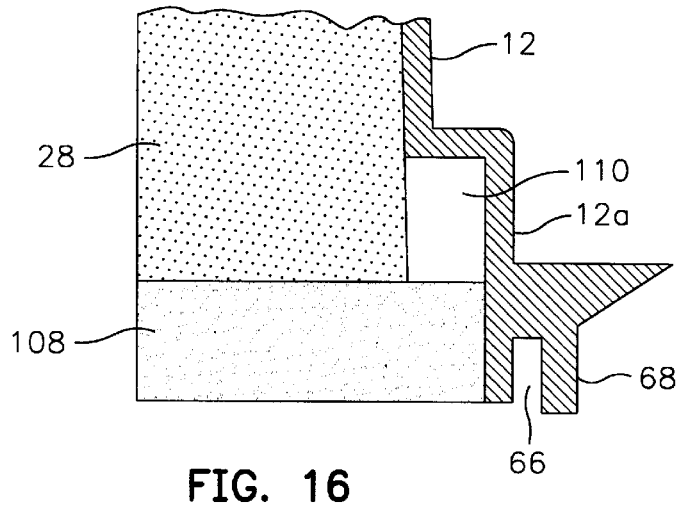
FIG. 16 is an enlarged view of a portion of FIG. 15 illustrating details of the blood outlet manifold of the blood oxygenator.
Figure 17:
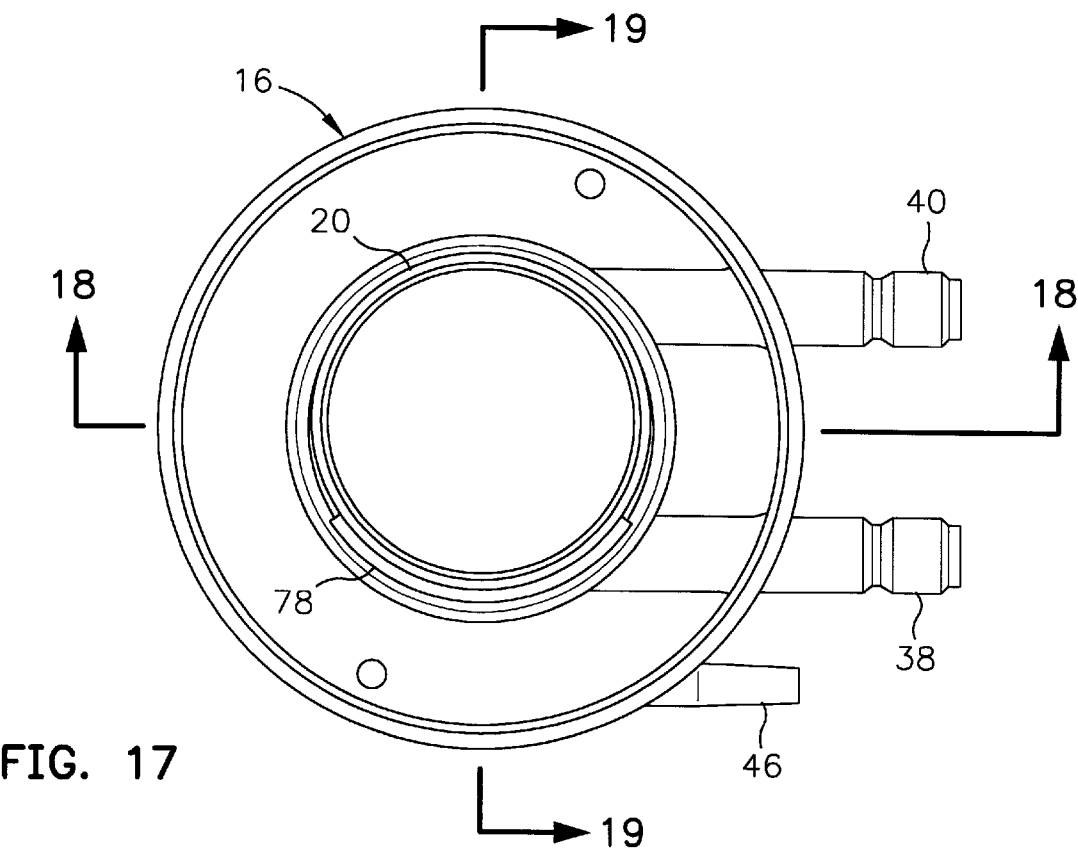
FIG. 17 is a top plan view of the lower venous gas header of the blood oxygenator. Also visible in this figure are the inner heat exchanger housing, the water inlet nozzle, the water outlet nozzle and the gas mixture outlet nozzle.
Figure 18:
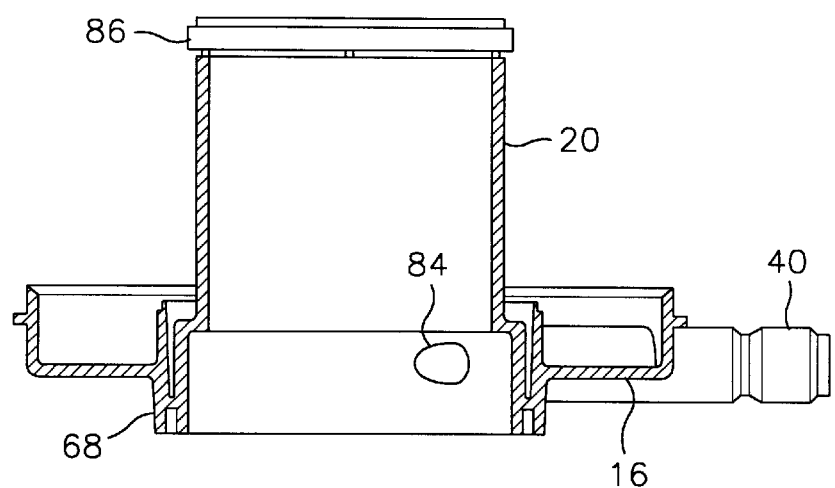
FIG. 18 is a sectional view of the lower venous gas header and inner heat exchanger housing taken along line 18—18 of FIG. 17.
Figure 19:
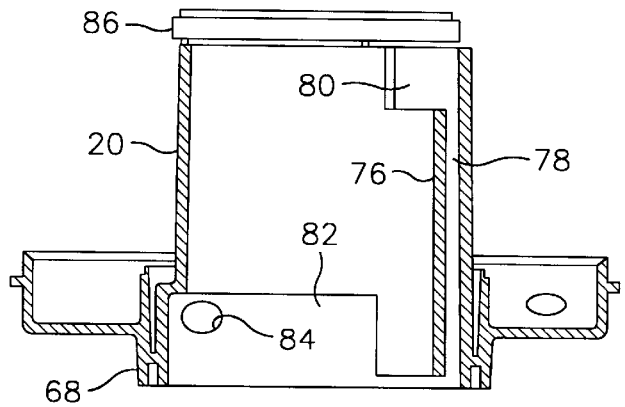
FIG. 19 is a sectional view of the lower venous gas header and inner heat exchanger housing taken along line 19—19 of FIG. 17.
Figure 20:
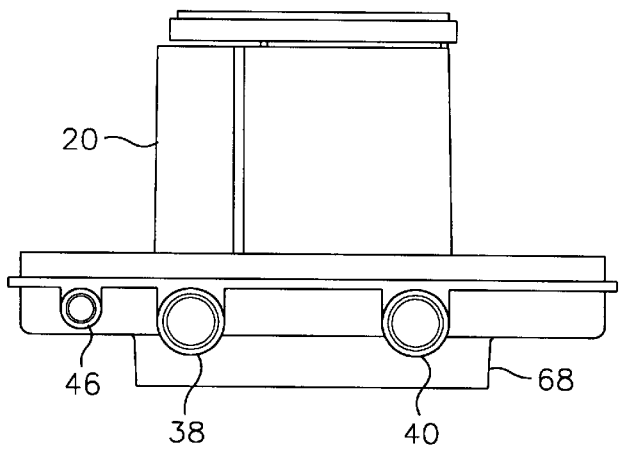
FIG. 20 is a front elevation view of the lower venous gas header and inner heat exchanger housing of the blood oxygenator.

Details of the blood inlet manifold 18 are illustrated in FIGS. 10–14. As previously indicated the blood inlet manifold 18 includes a barbed blood inlet nozzle 30. The nozzle 30 is connected to a piece of flexible elastomeric tubing (not illustrated) which carries oxygen-poor blood from the patient to the blood oxygenator 10. The blood inlet manifold 18 includes a generally conical wall member 60 having a circular vertical lip 62 and a horizontal annular rim 64 surrounding the periphery thereof. The circular vertical lip 62 is configured and dimensioned to be received in a downwardly opening vertical annular recess 66 (FIG. 16). The recess 66 is formed in a downwardly extending annular wall member 68. The wall member 68 is formed with, and projects from, the underside of the lower venous gas header 16. The interfitting relationship of the blood inlet manifold 18 and the raised annular wall member 68 is illustrated in FIG. 15. Preferably the conical wall member 60 (FIG. 10) extends at approximately a ten degree angle relative to a horizontal plane intersecting the vertical axis 70 of the blood oxygenator 10. This axis 70 is illustrated in phantom lines in FIG. 10.

The blood inlet nozzle 30 (FIG. 12) has a downstream segment 30a which extends at approximately a thirty degree angle relative to its upstream barbed segment 30b. The internal configuration of the upstream segment 30b is generally straight and tubular. The upstream segment 30b attaches directly to, and commmunicates with, the downstream segment 30a. The downstream segment 30a flares outwardly before exiting into the region boardered by the conical wall member 60 and the annular lip 62. A central vertical axis 72 (FIG. 12) of the downstream segment 30a of the inlet nozzle 30 is off center from the central vertical axis 70 (FIG. 10) of the conical wall member 60. A circular raised and pointed projection 74 (FIG. 14) extends upwardly from the outer periphery of the conical wall member 60. It is perferably positioned as close as possible to the co-planar lower ends of the micro-conduits 50 of the heat exchanger fiber bundle 26.

It will be understood that the configuration of the inlet manifold 18 (FIGS. 10–14) permits blood to be efficiently distributed from the tubing connected to the barbed nozzle segment 30b into the lower ends of the thousands of individual fibers 50 of the micro-conduit forming the heat exchanger fiber bundle 26. The thirty degree angle between the segments 30a and 30b of the blood inlet nozzle 30 permits the blood oxygenator to be located close to the floor of the surgery room. The tubing carrying the blood from patient can be connected to the barbed inlet segment 30b and can be gradually bent or curved in the horizontal direction, thereby minimizing the likelihood of kinking.

Figure 22:
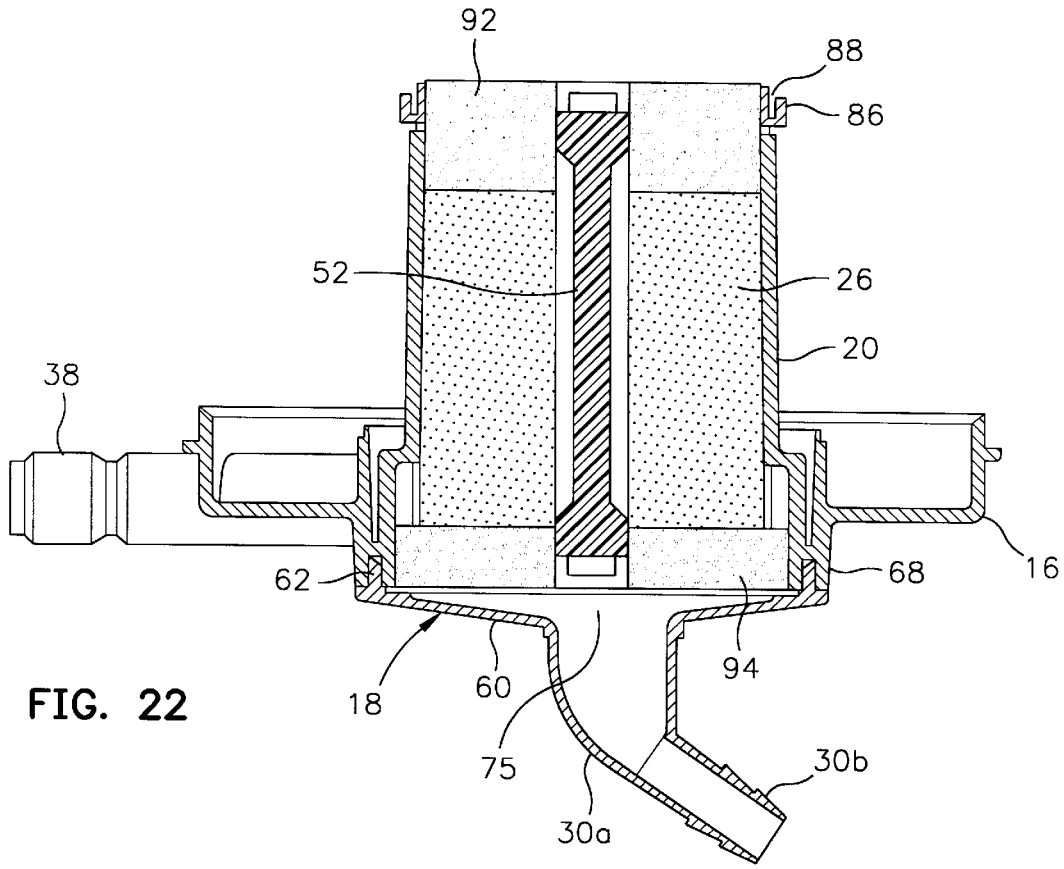
FIG. 22 is an enlarged vertical sectional view of the lower venous gas header and the inner heat exchanger housing with the blood inlet manifold connected thereto. Also illustrated in this view is the micro-conduit fiber bundle of the heat exchanger.

The geometry of the inlet manifold 18 (FIGS. 10–14) assures a uniform entry of blood into the thousands of fibers 50 that form the core of the heat exchanger. Non-uniform flow would essentially remove some of the heat exchange surface area from contact with blood. The heat exchanger fiber bundle 26 is compact, measuring, by way of example, approximately two and one-half inches in diameter. The internal diameter of the tubing connected to the barbed inlet segment 30b may be, for example, approximately 0.375 inches. Thus, in this example, the blood flood must diverge to almost seven times this diameter in order to uniformly fill the fibers 50 of the heat exchanger fiber bundle 26. The overall height of the blood inlet manifold 18 may be approximately one and seven-eights inches. The height of the circular vertical lip 62 is approximately five-sixteenths inches. In this example, the overall vertical height of the chamber 75 (FIG. 22) defined by the conical wall member 60 is about one-quarter of an inch. The upper and lower ends of the conduits 50 of the heat exchanger fiber bundle 26 terminate in co-planar fashion. The chamber 75 is bounded by the co-planar cut off lower ends of the micro-conduits 50 and the conical wall member 60. The blood inlet nozzle 30 and the conical wall member 60 arc configured and dimensioned to permit a blood flow rate of approximately five to seven liters per minute while minimizing shear forces and turbulances that would otherwise traumatize a significant number of cells and platelets in the blood.

The design of the configuration of the blood inlet manifold 30 was facilitated by a computer program based on computational fluid dynamics. The flared configuration of the upstream segment 30*a* (FIG. 12) of the inlet 30 helps to diverge the blood flow. The ten degree angle of the conical wall member 60 provides for efficient, uniform delivery of blood to the ends of the thousands of fibers of the heat exchanger fiber bundle 26. All this is accomplished with a minimum priming volume and in a manner that minimizes shear forces and recirculations, the presence of which can lead to unacceptable trauma of the blood cells or platelets, and clothing, respectively. The relatively flat angle, i.e., ten degrees, of the conical wall member 60 relative to a horizontal plane extending perpendicular to the vertical axis 70 helps to minimize the priming volume of the blood oxygenator and reduces the numbers and/or size of recirculations.

Figure 12:
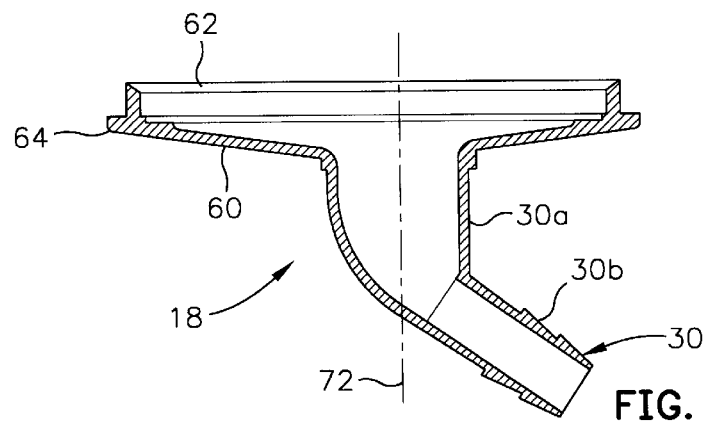
FIG. 12 is a vertical sectional view of the blood inlet manifold of the blood oxygenator taken along line 12—12 of FIG. 11.
Figure 13:
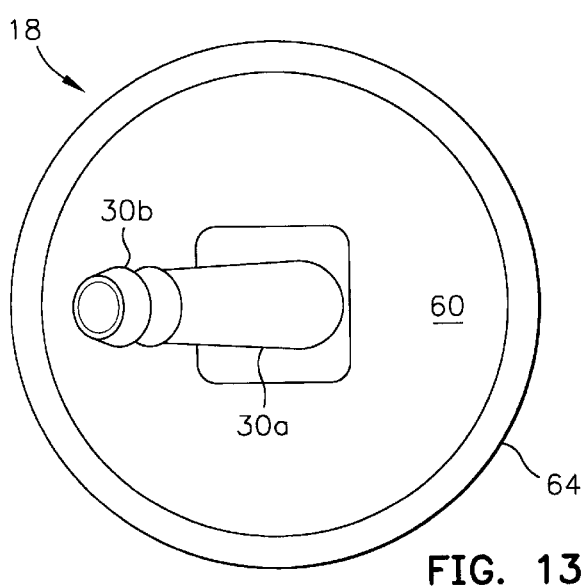
FIG. 13 is a top plan view of the blood inlet manifold of the blood oxygenator.
Figure 14:
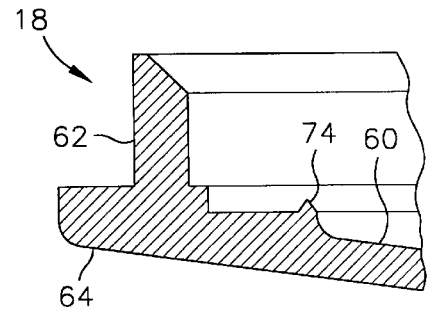
FIG. 14 is a further enlarged, fragmentary vertical sectional view of illustrating portions of the conical wall member, vertical lip and rim of the blood inlet manifold of the blood oxygenator of FIGS. 10–13.

Referring to FIG. 12, it can be seen that one side of the upstream segment 30*a* of the blood inlet 30 is vertical, while the other side follows a complex curve. The misalignment between the center of the inlet segment 30*a* and the vertical axis 70 has been shown, through computer modeling, to help achieve uniform flow with reduces eddies.

The configuration of the lower venous gas header 16, the inner heat exchanger housing 20, the water inlet and outlet nozzles 38 and 40 and the gas mixture outlet nozzle 46, are illustrated in FIGS. 17–21. These parts, along with the raised annular wall member 68 that receives the blood inlet manifold 18, are all injection molded as a single unitary piece of plastic. The inner heat exchanger housing 20 is formed with an interior vertical wall member 76 (FIG. 19) that defines a water flow channel or path 78 (FIGS. 17 and 19) which extends vertically along one side of the heat exchanger housing 20. The lower end of the water flow path 78 communicates with the interior of the water inlet nozzle 38. The upper end of the water flow path 78 communicates through a port 80 (FIG. 19) into the upper interior of the housing 20. This permits the incoming heat exchange water to be disbursed around the upper ends of the thousands of micro-conduits or fibers 50 of the heat exchanger fiber bundle 26. As previously explained, this water flows downwardly around the outside of the fibers 50, through another port 82, and then out through water outlet nozzle 40. The opening of the nozzle 40 is shown at 84 in FIG. 19.

Figure 21:
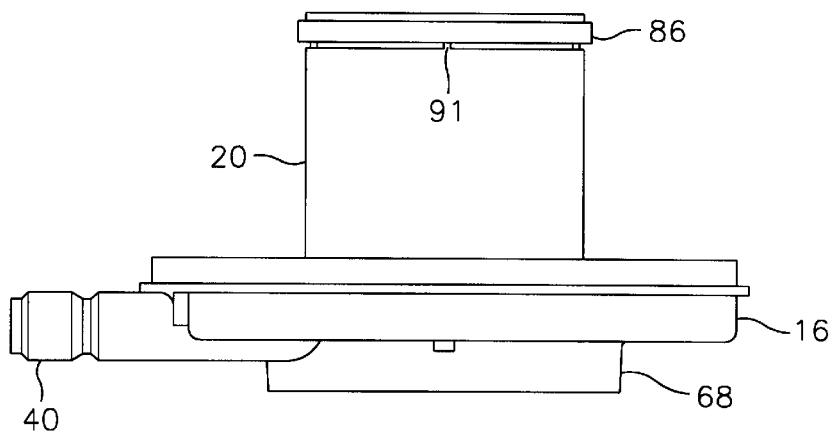
FIG. 21 is a side elevation view of the lower venous gas header and inner heat exchanger housing of the blood oxygenator.

The upper end of the cylindrical heat exchanger housing 20 is molded with a fitting ring 86 (FIGS. 19 and 21) having an upwardly opening circular recess 88 (FIG. 22) for receiving, and interfitting with, a downwardly extending circular flange 90 (FIG. 24) of the outer heat exchanger housing 22. The fitting ring 86 is connected to the main part of the housing 20 by small plastic extensions 91 (FIG. 21).

The heat exchanger portion of the blood oxygenator 10 is manufactured in accordance with the following general process. First the micro-conduit wrapping material is wound about the spindle 52 to form the generally cylindrical fiber bundle 26. This fiber bundle is then inserted inside the inner heat exchanger housing 20. Generally disc-shaped bodies 92 and 94 (FIG. 22) of a suitable urethane potting compound are formed at the upper and lower ends of the fiber bundle 26. The potting compound disperses around and between the thousands of fibers at each end. The potting compound also bonds to the inner surface of the housing 20 and to the spindle 52. The bodies 92 and 94 of potting compound therefore form upper and lower water-tight seals. Once the upper and lower seals 92 and 94 have been formed inside the inner heat exchanger housing 20, the ends of the fiber bundle 26 are cleanly cut off in co-planar fashion in order to open the upper and lower ends of the thousands of micro-conduits or fibers 50 in the fiber bundle 26. A suitable wetting agent is preferably applied to the interior surfaces of the micro-conduits or fibers 50 of the fiber bundle 26 as previously indicated. This is done before joining heat exchanger with remaining components of the blood oxygenator.

The reason for providing the seals 92 and 94 is as follows. The water flow passage 78 introduces water into the top of the fiber bundle 26 below the upper seal 92. This water flows downwardly through the fiber bundle 26 around and across the exterior surfaces of the fibers 50 which carry blood upwardly in their minuet hollow interiors. The water exits through the outlet nozzle 40 which communicates with the fiber bundle 26 above the lower seal 94. Thus the seals 92 and 94 formed by the urethane potting compound prevent the inter-mixing of blood water. Where the fibers 50 of the heat exchanger fiber bundle 26 are made of polyethylene or polypropylene, it is desirable to surface treat their ends, e.g. with a corona discharge, in order to enhance the bond between the fibers and the urethane bonding material. Further details of this treatment are described in co-pending U.S. patent application Ser. No. 08/585,323 filed on Jan. 11, 1996 entitled SURFACE TREATMENT FOR MICRO-CONDUITS EMPLOYED IN BLOOD HEAT EXCHANGE SYSTEM. Said application is also assigned to Medtronic, Inc. of Minneapolis, Minn., U.S.A. The entire disclosure of the aforementioned patent application is specifically incorporated by reference.

Figure 23:
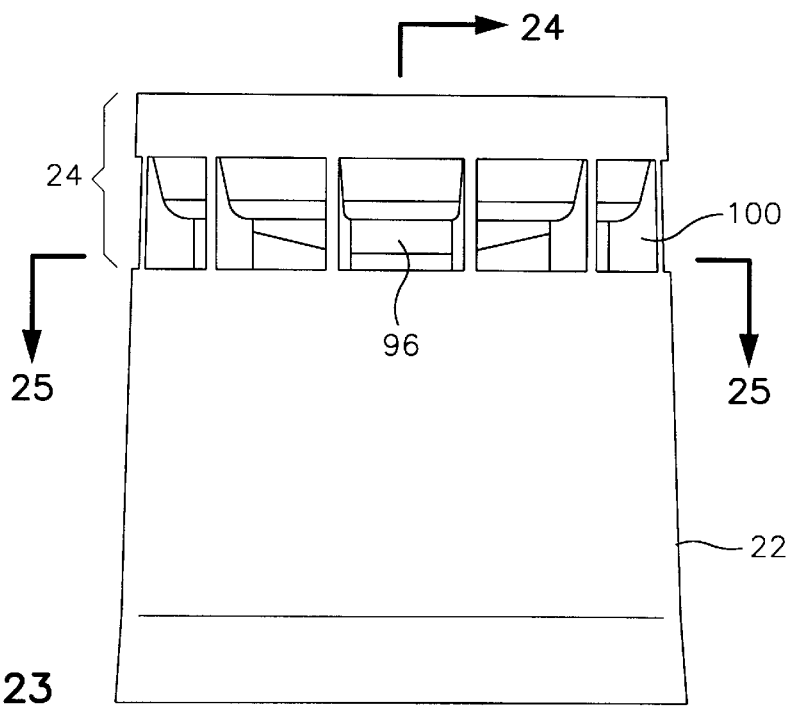
FIG. 23 is an enlarged side elevation view of the outer heat exchanger housing and the transition manifold.
Figure 24:
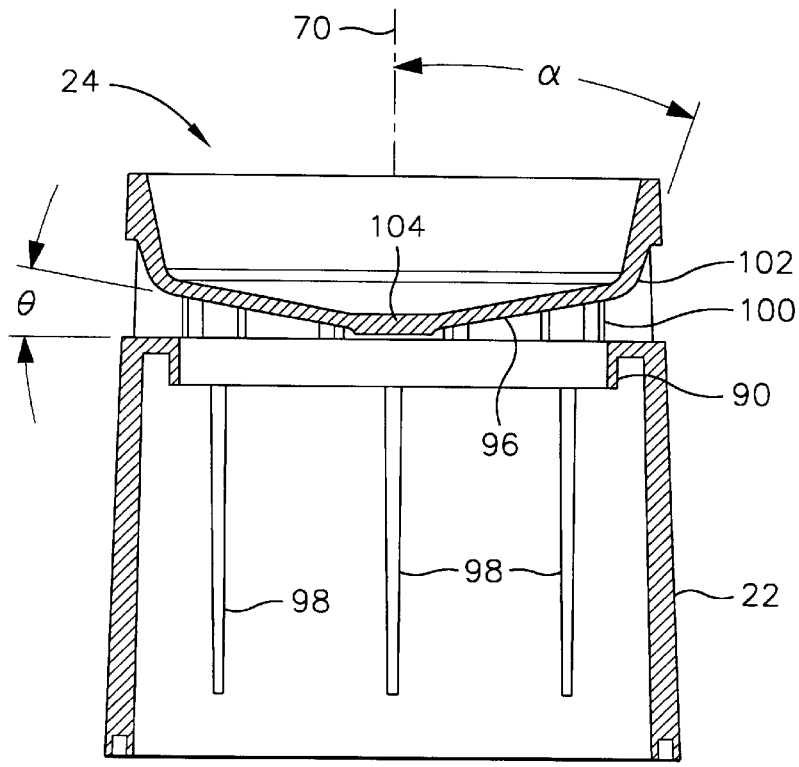
FIG. 24 is a vertical sectional view of the outer heat exchanger housing and the transition manifold taken along line 24—24 of FIG. 23.
Figure 25:
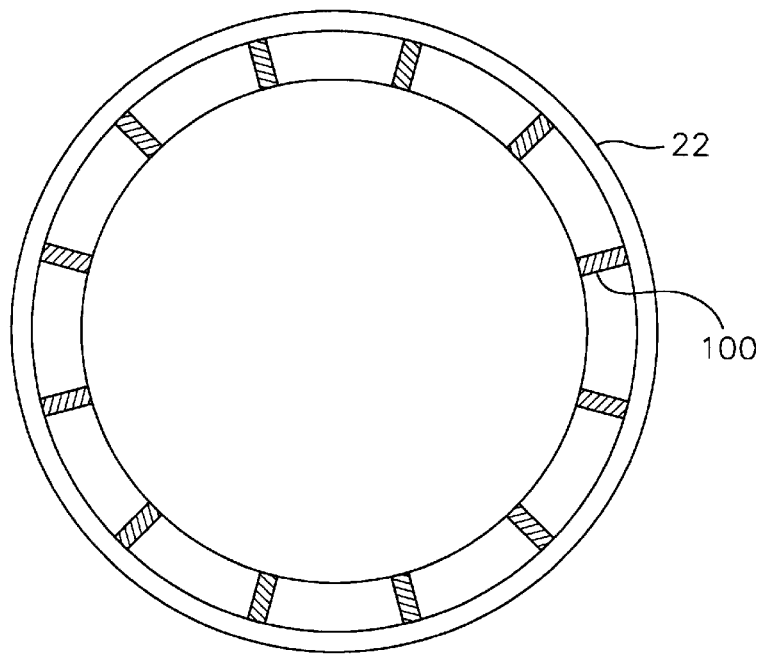
FIG. 25 is a horizontal sectional view of the outer heat exchanger housing and transition manifold taken along line 25—25 of FIG. 23.

FIGS. 23–26 illustrate details of the outer heat exchanger housing 22. The housing 22 comprises a generally cylindrical body which incorporates at its upper end a transition manifold 24 including a generally conical wall member 96. The housing 22 has a diameter and height which are selected so that the housing 22 can fit and around, in concentric fashion, the inner heat exchanger housing 20 as best seen in FIGS. 1 and 15. The housing 22 actually is slightly frusto-conical in shape, like vessel 12. Its vertical side wall is slightly tapered, e.g. two degrees. This draft is beneficial when injection molding these components to facilitate ejection from the molding tools. The interior surface of the housing 22 is formed with a plurality of circumferentially spaced, vertically extending tapered ribs 98 (FIG 24).

As previously indicated, the outer heat exchanger housing 22 is formed at its upper end with a circular, downwardly extending flange 90 (FIG. 24) which interfits with, and is received in, and upwardly opening recess 88 in the fitting ring 86 formed at the upper end of the inner heat exchanger housing 20. The transition manifold 24 includes the generally conical wall member 96 (FIGS. 23 and 24). It further includes a plurality of radially extending vertical fins 100. The fins 100 are spaced circumferentially about the upper end of the housing 22 and serve to support and connect the conical wall member 96 with the upper end of the main cylindrically shell portion of outer heat exchanger. As illustrated diagrammatically in FIG. 4, the transition manifold 24 serves to redirect the upwardly flowing blood from the micro-conduits or fibers 50 of the heat exchanger fiber bundle 26 radially outwardly around the micro-porous fibers 48 of the oxygenator fiber bundle 28.

The configuration of the transition manifold 24 was also optimized by executing a computer program based on computational fluid dynamics. The configuration of the transition manifold is designed to achieve a uniform distribution of blood flowing out of the heat exchanger fiber bundle 26 into the oxygenator fiber bundle 28, with a minimum of shear forces exerted on the blood cells and platelets. At the same time, the transition manifold 24 enables the blood oxygenator configuration to remain compact, and does not unduly increase the blood volume of the blood oxygenator. Furthermore, the configuration of the transition manifold 24 minimizes shear forces that would otherwise traumatize the blood cells and platelets. It also minimizes re-circulations and stagnant areas that could lead to clotting.

In the preferred embodiment 10 of the blood oxygenator of the present invention, the angle θ (FIG. 24) between the conical wall member 96 and a horizontal plane intersecting the vertical axis 70 is approximately eleven and one half degrees. The transition manifold 24 further includes an upwardly tapered wall section 102 which is circular and is located radially outward from the conical wall member 96. The angle α between the surface of the wall section 102 and the vertical axis 70 is approximately fourteen degrees. The angles θ and α of the wall member 96 and wall section 102 are specifically designed to eliminate recirculations. They also minimizes shear forces. The conical wall member 96 includes a central downwardly projecting boss or hub 104 (FIG. 24). This hub 104 has a round configuration and is generally positioned over the center of the heat exchanger fiber bundle 26, adjacent the upper end of its spindle 52. The upper end of the spindle 52 is covered by potting compound. Preferably the hub 104 is positioned as close as possible to the potting compound above the spindle 52 to eliminate a stagnant region that would otherwise exist.

Referring to FIGS. 1 and 15, the ring-shaped oxygenator fiber bundle 28 concentrically surrounds the outer heat exchanger housing 22. After the bundle 28 is wound about the housing 22 both components are inserted inside the vessel 12. Upper and lower generally ring-shaped seals 106 and 108 (FIG. 15), respectively, are then formed by introducing a urethane potting compound around the upper and lower ends of the fibers 48 of the oxygenator fiber bundle 28. These seals prevent the blood from flowing into the upper and lower venous gas headers 14 and 16. Thereafter, the upper and lower ends of the fibers 48 are cleaning cut-off to allow the upper and lower hollow interiors of these fibers to communicate with the interior of the upper and lower hollow venous gas headers 14 and 16.

The blood oxygenator 10 of the present invention incorporates a specially configured annular blood outlet manifold for collecting the blood from around the fibers 48 at the lower end of the oxygenator fiber bundle 28. More specifically, the flared portion 12a of the vessel 12 (FIGS. 1 and 2) provides an annular blood collection chamber 110 (FIG. 16) for collection of the blood and routing of the same through the blood outlet nozzle 32. The chamber 110 has a generally rectangular cross-section, the precise dimensions and configuration of which were determined by executing a computer program based on computational fluid dynamics. The configuration of the blood outlet manifold was designed to uniformly collect blood from the lower portion of the oxygenator fiber bundle 28 and to efficiently route the blood through the blood outlet nozzle 32 with a minimum of shear forces and recirculations. The blood collection chamber 110 (FIG. 15) is formed between the lower outside surface of the oxygenator fiber bundle 28 and the inner wall of the flared portion 12a of the vessel 12.

The vessel 12, and housings 20 and 22 have been described as being generally cylindrical. They actually have a slight degree of taper, e.g. two degrees. In other words, the vertical sidewalls of these structures diverge slightly moving in a downward direction. Thus, it will be understood that the use of the term "generally cylindrical" herein includes minor deviations from perfectly cylindrical.

Except for the fiber bundles 26 and 28, and the potting compound comprising the seals 92, 94, 106 and 108, the remainder of the structures illustrated and described herein are preferably injection molded of clear polycarbonate plastic. Suitable plastics are commercially available under the designations BAYER Makrolon and General Electric LEXAN HP2r-1112. The separately molded plastic components may be assembled and permanently affixed to each other with a suitable non-toxic ultraviolet (UV) curable adhesive.

Having described a blood oxygenator incorporating a preferred embodiment of the present invention, it will occur to those of ordinary skill in the art that the preferred embodiment can be modified in both arrangement and detail while still embodying said invention. Accordingly, the protection afforded the subject invention should only be limited in accordance with the following claims.

What is claimed is:

1. A transition manifold for use in association with the upper end of a generally cylindrical heat exchanger fiber bundle having a plurality of vertically extending conduits with open upper ends terminating in substantially co-planar fashion, comprising:

a generally conical wall member defining a surface extending at a relatively flat angle with respect to a plane perpendicular to a vertical central axis of the heat exchanger fiber bundle and diverging away from the upper end of the heat exchanger fiber bundle in a direction moving radially outwardly from the central axis for redirecting blood flowing vertically upwardly from the open upper ends of the conduits of the heat exchanger fiber bundle in a radially outward direction substantially uniformly around an upper portion of a generally cylindrical oxygenator fiber bundle surrounding the heat exchanger fiber bundle;

a hub projecting downwardly from a center of the conical wall member and configured to substantially eliminate a stagnant blood flow region that would otherwise exist above a center of the upper end of the heat exchanger fiber bundle;

a housing connected to the conical wall member for supporting the conical wall member centrally above the upper end of the heat exchanger fiber bundle; and a circular flange joined to, and extending downwardly from, an upper end of the housing for mating with an inner heat exchanger housing.

2. A transition manifold according to claim 1 and further comprising a plurality of vertically extending radially oriented fins connecting the housing and the conical wall member, the fins being equally spaced around a circumference of the conical wall member.

3. A transition manifold according to claim 2 wherein each one of the fins extends at an angle of approximately thirty degrees relative to an adjacent fin.

4. A transition manifold according to claim 1 wherein a circular upwardly tapered wall section is joined to an outer periphery of the conical wall member, the wall section having a face that diverges upwardly at a second angle relative to the vertical central axis away from the surface of the conical wall member.

5. A transition manifold according to claim 4 wherein the second angle is approximately fourteen degrees.

6. A transition manifold according to claim 4 wherein the flat angle is approximately eleven and one-half degrees and the second angle is approximately fourteen degrees.

7. A transition manifold according to claim 1 wherein the flat angle is approximately eleven and one-half degrees.

* * * * *